(12) United States Patent
Chuang et al.

(10) Patent No.: US 10,858,471 B2
(45) Date of Patent: Dec. 8, 2020

(54) REVERSIBLE CROSSLINKING REACTANT COMPOSITION

(71) Applicant: Industrial Technology Research Institute, Hsinchu (TW)

(72) Inventors: Kuei-Yi Chuang, Hsinchu (TW); Kuo-Chan Chiou, Tainan (TW); Feng-Po Tseng, Taoyuan (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 0 days.

(21) Appl. No.: 16/179,170

(22) Filed: Nov. 2, 2018

(65) Prior Publication Data

US 2019/0153139 A1  May 23, 2019

Related U.S. Application Data

(60) Provisional application No. 62/580,483, filed on Nov. 2, 2017.

(51) Int. Cl.

| | | |
|---|---|---|
| *C08F 277/00* | (2006.01) | |
| *C08L 101/06* | (2006.01) | |
| *C08G 73/06* | (2006.01) | |
| *C08G 65/40* | (2006.01) | |
| *C08G 73/12* | (2006.01) | |
| *C08G 65/44* | (2006.01) | |
| *C08L 71/00* | (2006.01) | |
| *C08L 71/12* | (2006.01) | |
| *C07D 307/42* | (2006.01) | |
| *C07D 307/52* | (2006.01) | |
| *C07D 407/06* | (2006.01) | |
| *C08G 18/02* | (2006.01) | |
| *C08G 18/83* | (2006.01) | |
| *C08G 61/04* | (2006.01) | |
| *C08G 61/10* | (2006.01) | |
| *C08G 61/12* | (2006.01) | |
| *C08G 65/331* | (2006.01) | |
| *C08F 267/04* | (2006.01) | |
| *C08F 283/08* | (2006.01) | |
| *C08F 283/10* | (2006.01) | |
| *C08F 299/02* | (2006.01) | |

(52) U.S. Cl.
CPC .......... *C08F 277/00* (2013.01); *C07D 307/42* (2013.01); *C07D 307/52* (2013.01); *C07D 407/06* (2013.01); *C08F 267/04* (2013.01); *C08F 283/08* (2013.01); *C08F 283/10* (2013.01); *C08F 299/022* (2013.01); *C08G 18/022* (2013.01); *C08G 18/831* (2013.01); *C08G 61/04* (2013.01); *C08G 61/10* (2013.01); *C08G 61/124* (2013.01); *C08G 65/3318* (2013.01); *C08G 65/40* (2013.01); *C08G 65/44* (2013.01); *C08G 73/0655* (2013.01); *C08G 73/126* (2013.01); *C08L 71/00* (2013.01); *C08L 71/126* (2013.01); *C08L 101/06* (2013.01); *C08F 2500/02* (2013.01); *C08F 2810/40* (2013.01); *C08G 2261/149* (2013.01); *C08G 2261/1646* (2013.01)

(58) Field of Classification Search
CPC .... C08F 277/00; C08F 283/08; C08F 283/10; C08F 267/04; C08F 299/022; C08F 2500/02; C08F 2810/40
See application file for complete search history.

(56) References Cited

U.S. PATENT DOCUMENTS

| | | |
|---|---|---|
| 3,435,003 A | 3/1969 | Craven |
| 9,012,127 B2 | 4/2015 | Bowman et al. |
| 9,085,719 B2 | 7/2015 | Boday et al. |
| 2013/0059988 A1 | 3/2013 | Palmese et al. |
| 2017/0226271 A1 | 8/2017 | Makal et al. |
| 2017/0240493 A1 | 8/2017 | Kennedy et al. |

FOREIGN PATENT DOCUMENTS

| | | |
|---|---|---|
| CN | 102803416 A | 11/2012 |
| EP | 0 357 110 A1 | 3/1990 |

(Continued)

OTHER PUBLICATIONS

Japanese Office Action for Appl. No. 2018-207712 dated Oct. 23, 2019 (w/ English translation).

(Continued)

*Primary Examiner* — Shane Fang
(74) *Attorney, Agent, or Firm* — Birch, Stewart, Kolasch & Birch, LLP

(57) ABSTRACT

A reversible crosslinking reactant composition is provided. The composition includes at least one furan-group-containing oligomer having a structure represented by Formula (I) and a bismaleimide compound having a structure represented by

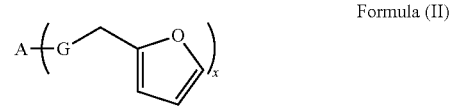
Formula (II)

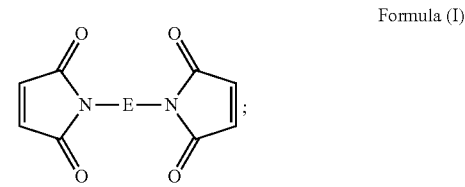

Formula (I)

Formula (II), wherein the equivalent ratio of the furan group of the furan-group-containing oligomer having a structure represented by Formula (I) to the maleimide group of the bismaleimide compound having a structure represented by Formula (II) is from 0.5:1 to 1:0.5.

11 Claims, No Drawings

(56) References Cited

FOREIGN PATENT DOCUMENTS

| JP | H2-88613 A | 3/1990 |
|----|---|---|
| JP | 2006-335861 A | 12/2006 |
| JP | 2012-530150 A | 11/2012 |
| JP | 2019-85409 A | 6/2019 |
| TW | 201609848 A | 3/2016 |
| WO | WO 2012/074994 A1 | 6/2012 |
| WO | WO 2016/018956 A1 | 2/2016 |

OTHER PUBLICATIONS

Extended European Search Report dated Apr. 5, 2019 for Application No. 18204154.1.
Shibata et al., "High-Performance Hybrid Materials Prepared by the Thermo-Reversible Diels-Alder Polymerization of Furfuryl Ester-Terminated Butylene Succinate Oligomers and Maleimide Compounds", Polymer Journal, vol. 43, 2011 (published online Mar. 2, 2011), pp. 455-463.
Taiwanese Office Action and Search Report for Taiwanese Application No. 107138967, dated Mar. 27, 2020.

REVERSIBLE CROSSLINKING REACTANT COMPOSITION

CROSS REFERENCE TO RELATED APPLICATIONS

This application claims the benefit of U.S. Provisional Application No. 62/580,483, filed on Nov. 2, 2017, which is hereby incorporated by reference herein.

TECHNICAL FIELD

The technical field relates to a reversible crosslinking reactant composition.

BACKGROUND

In end of 2015, European union published Circular Economy Package (CEP). The compositions and components of products in future should meet the requirements of being repairable, durable, and recyclable to achieve circular economy. In addition, the Paris Agreement in 2016 proposed to reduce greenhouse gas emission and keeping a global average temperature below 2° C. above pre-industrial levels.

Of the elements of conventional electronic products, printed circuit boards (PCBs) are responsible for the most $CO_2$ emissions, e.g. over 100000 kg $CO_2$/10000 $m^2$ PCB. As such, the related industries are encountering the challenges of efficiently recycling waste PCBs to lower $CO_2$ emissions, while simultaneously obeying the energy related ecodesign directives. The conventional method of recycling a waste PCB is to crush it and then purifying or burying the metal and plastic in a landfill. However, the recycling ratio is usually lower than 3%. Therefore, in practice, waste PCBs still get incinerated, which may produce a lot of $CO_2$ and contribute to the greenhouse effect. The skill of purifying metal has matured in recent years, and 130 kg of copper, 19 kg of tin, and about 16 ounce of gold can be refined from 1 ton of PCBs today. However, a PCB contains about 54.5% of plastic, which is the major $CO_2$ emission source. The plastic in a PCB includes insulation resin and glass fiber cloth. All the conventional resin systems for PCBs belong to thermosetting polymer, which has stable properties and is therefore difficult to recycle. Although decomposable thermoplastic polymer is provided, the glass transfer temperature, the thermal cracking temperature, and the flame resistance of the thermoplastic polymer should be improved even further, in order to achieve the properties of the conventional insulation resin in PCB.

Not only the PCB, the resin composition used in other products that need to withstand high temperatures during process or use also encounters the similar challenge when the demands of recycling wastes is increased.

SUMMARY

According to embodiments of the disclosure, the disclosure provides a reversible crosslinking reactant composition. The reversible crosslinking reactant composition includes at least one furan-group-containing oligomer having a structure represented by Formula (I) and a bismaleimide compound having a structure represented by Formula (II):

Formula (I)

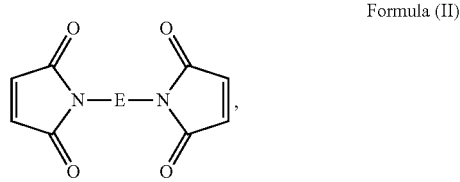

Formula (II)

wherein the equivalent ratio of the furan group of the furan-group-containing oligomer having a structure represented by Formula (I) to the maleimide group of the bismaleimide compound having a structure represented by Formula (II) is from 0.5:1 to 1:0.5.

In Formula (I), x is an integer of 1 to 5, A is a repeating unit containing amine group, amide group, imide group, ester group, phenyl ether group, or enol ether group, G is a bonding, —O—, —NH—, —Ar—NH—$(CH_2)_b$—, —Ar—O—$(CH_2)_b$—, —Ar—O—$(CH_2)_a$—NH—$(CH_2)_b$—, —$(CH_2)_a$—NH—$(CH_2)_b$—, —$(CH_2)_a$—O—$(CH_2)_b$—, or —$(CH_2)_a$—CH(OH)—$(CH_2)_b$—NH—, Ar is substituted or unsubstituted arylene group, a is an integer of 1 to 5, and b is an integer of 0 to 5. The furan-group-containing oligomer having a structure represented by Formula (I) has a number average molecular weight from 1000 to 12000.

In Formula (II), E is substituted or unsubstituted $C_6$-$C_{25}$ arylene group, $C_7$-$C_{25}$ alkyl aryl group, $C_7$-$C_{25}$ arylalkyl group, $C_6$-$C_{25}$ heteroarylene group, $C_7$-$C_{25}$ acylaryl group, $C_7$-$C_{25}$ alkoxyaryl group, $C_7$-$C_{25}$ acyloxyaryl group, $C_6$-$C_{25}$ arylene ether group, or $C_6$-$C_{25}$ arylene ether group.

According to embodiments of the disclosure, the disclosure provides a reversible crosslinking reactant composition, including an oligomer, wherein the oligomer has a number average molecular weight of 1000 to 12000, wherein the oligomer is an oligomer having a structure represented by Formula (IV), an oligomer having a structure represented by Formula (V), or an oligomer having a first repeating unit and a second repeating unit, wherein the first repeating unit has a structure represented by Formula (VI), the second repeating unit has a structure represented by Formula (VII), and the first repeating unit and the second repeating unit are arranged randomly or in blocks, Formula (IV)

-continued

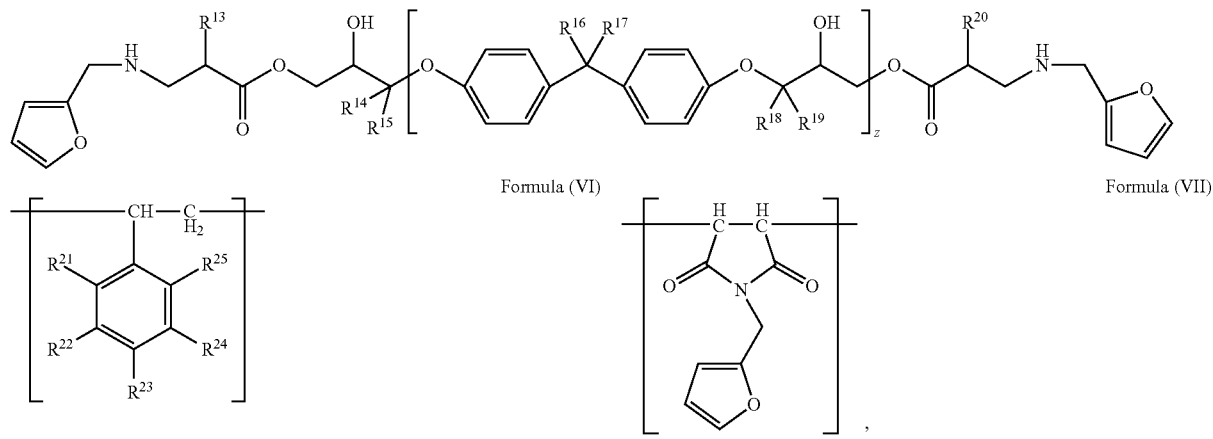

Formula (V)

Formula (VI)

Formula (VII)

wherein each of $R^1$, $R^2$, $R^3$, $R^4$, $R^5$, $R^6$, $R^7$, $R^8$, $R^9$, $R^{10}$, $R^{11}$, and $R^{12}$ is independently hydrogen, $C_{1-6}$ alkyl group, $C_{1-6}$ alkoxy group, or halogen; each of $R^{13}$, $R^{14}$, $R^{15}$, $R^{18}$, $R^{19}$, and $R^{20}$ is independently hydrogen or $C_{1-6}$ alkyl group; each of $R^{16}$ and $R^{17}$ is independently hydrogen, $C_{1-6}$ alkyl group, $C_{5-8}$ cycloalkyl group, $C_{6-12}$ aryl group, $C_5$-$C_{10}$ heteroaryl group, or halogen; each of $R^{21}$, $R^{22}$, $R^{23}$, $R^{24}$, and $R^{25}$ is independently hydrogen, $C_{1-6}$ alkyl group, or halogen; q is an integer of 5 to 50; and z is an integer of 5 to 20; and a bismaleimide compound having a structure represented by Formula (II):

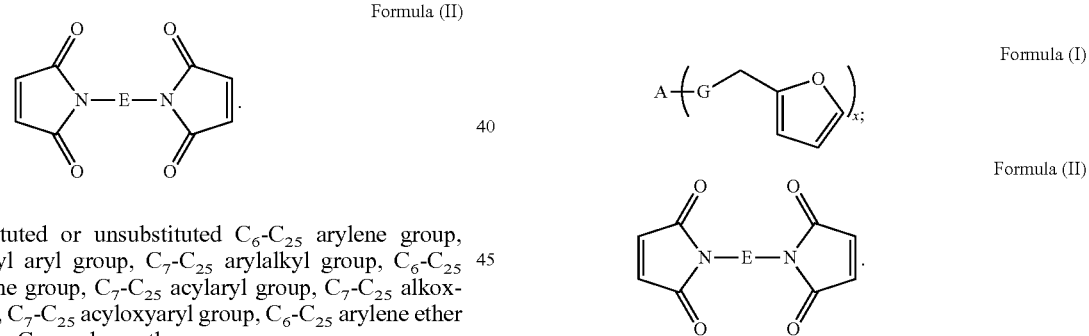

Formula (II)

E is substituted or unsubstituted $C_6$-$C_{25}$ arylene group, $C_7$-$C_{25}$ alkyl aryl group, $C_7$-$C_{25}$ arylalkyl group, $C_6$-$C_{25}$ heteroarylene group, $C_7$-$C_{25}$ acylaryl group, $C_7$-$C_{25}$ alkoxyaryl group, $C_7$-$C_{25}$ acyloxyaryl group, $C_6$-$C_{25}$ arylene ether group, or $C_6$-$C_{25}$ arylene ether group.

A detailed description is given in the following embodiments.

DETAILED DESCRIPTION

Embodiments of the disclosure provide a reversible crosslinking reactant composition.

The furan group of the oligomer and the maleimide group of the bismaleimide compound in the composition will crosslink through 1,2-addition at a suitable temperature. The crosslink bonding will be broken by reverse reaction at another suitable temperature, such that the bridge between the furan-group-containing oligomer/compound and the bismaleimide compound is broken. As such, the furan-group-containing oligomer/compound and the bismaleimide compound are recovered back to original non-cross-linked state, thereby being beneficial to recycle and reuse the composition. If the furan-group-containing oligomer has a specific structure, it will be cross-linked with the bismaleimide compound at a temperature of 80° C. to 150° C. Furthermore, the cross-linked composition will reverse to non-cross-linked state through a reverse crosslinking reaction when the temperature is larger than 200° C. Accordingly, the composition can be applied as a raw material related to photoelectric or communication products requiring high-temperature processes.

According to embodiments of the disclosure, the disclosure provides a reversible crosslinking reactant composition. The reversible crosslinking reactant composition includes at least one furan-group-containing oligomer having a structure represented by Formula (I) and a bismaleimide compound having a structure represented by Formula (II):

Formula (I)

Formula (II)

The equivalent ratio of the furan group of the furan-group-containing oligomer having a structure represented by Formula (I) to the maleimide group of the bismaleimide compound having a structure represented by Formula (II) is from 0.5:1 to 1:0.5.

In Formula (I), x is an integer of 1 to 5, A is a repeating unit containing amine group, amide group, imide group, ester group, phenyl ether group, or enol ether group, G is a bonding, —O—, —NH—, —Ar—NH—$(CH_2)_b$—, —Ar—O—$(CH_2)_b$—, —Ar—O—$(CH_2)_a$—NH—$(CH_2)_b$—, —$(CH_2)_a$—NH—$(CH_2)_b$—, —$(CH_2)_a$—O—$(CH_2)_b$—, or —$(CH_2)_a$—CH(OH)—$(CH_2)_b$—NH—, Ar is substituted or unsubstituted arylene group, a is an integer of 1 to 5, and b is an integer of 0 to 5. The furan-group-containing oligomer having a structure represented by Formula (I) has a number average molecular weight of 1000 to 12000.

In Formula (II), E is substituted or unsubstituted $C_6$-$C_{25}$ arylene group, $C_7$-$C_{25}$ alkyl aryl group, $C_7$-$C_{25}$ arylalkyl group, $C_6$-$C_{25}$ heteroarylene group, $C_7$-$C_{25}$ acylaryl group, $C_7$-$C_{25}$ alkoxyaryl group, $C_7$-$C_{25}$ acyloxyaryl group, $C_6$-$C_{25}$ arylene ether group, or $C_6$-$C_{25}$ arylene ether group.

In some embodiments of the disclosure, Ar is substituted or unsubstituted phenylene group, biphenylene group, naphthylene group, thienylene group, indolylene group, phenanthrenylene, indenylene group, anthracenylene group, or fluorenylene group. More specifically, Ar is phenylene group, biphenylene group, naphthylene group, thienylene group, indolylene group, phenanthrenylene, indenylene group, anthracenylene group, or fluorenylene group with substitution groups of one to four $C_1$-$C_6$ alkyl groups.

In some embodiments of the disclosure, A is

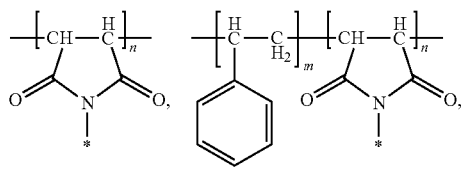

in which the repeating unit

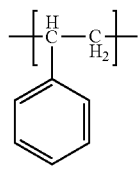

and the repeating unit

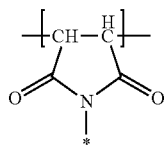

are arranged in order or random, wherein A is connected to G by the location represented by *, m is an integer of 7 to 200, n is an integer of 7 to 200, each of p, r, and s is an integer of 1 to 5, q is an integer of 5 to 50, z is an integer of 5 to 20, each of $R_1$, $R_2$, $R_3$, and $R_4$ is independently $C_1$-$C_5$ alkyl group, $T_1$ is a bonding, $C_1$-$C_{12}$ linear or branched alkyl group, —O—, —S—, or —NH—, Q is

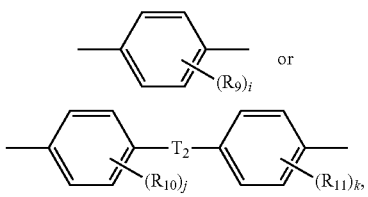

wherein each of $R_9$, $R_{10}$, and $R_{11}$ is independently $CH_3$ or $C_2H_5$, $T_2$ is $C_1$-$C_{12}$ linear or branched alkyl group, and each of I, j, and k is an integer of 1 to 5.

In some embodiments of the disclosure, E in Formula (II) is

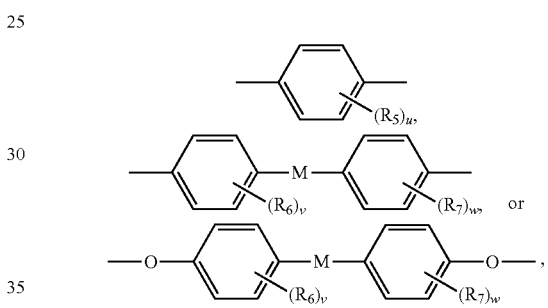

wherein each of u, v, and w is an integer of 1 to 5, each of $R_5$, $R_6$, and $R_7$ is independently $C_1$-$C_5$ alkyl group, M is a bonding, —O—, —S—, or $C_1$-$C_{12}$ linear or branched alkyl group, and p is an integer of 1 to 4.

In some embodiments of the disclosure, the reversible crosslinking reactant composition further includes a furan-group-containing compound having a structure represented by Formula (III):

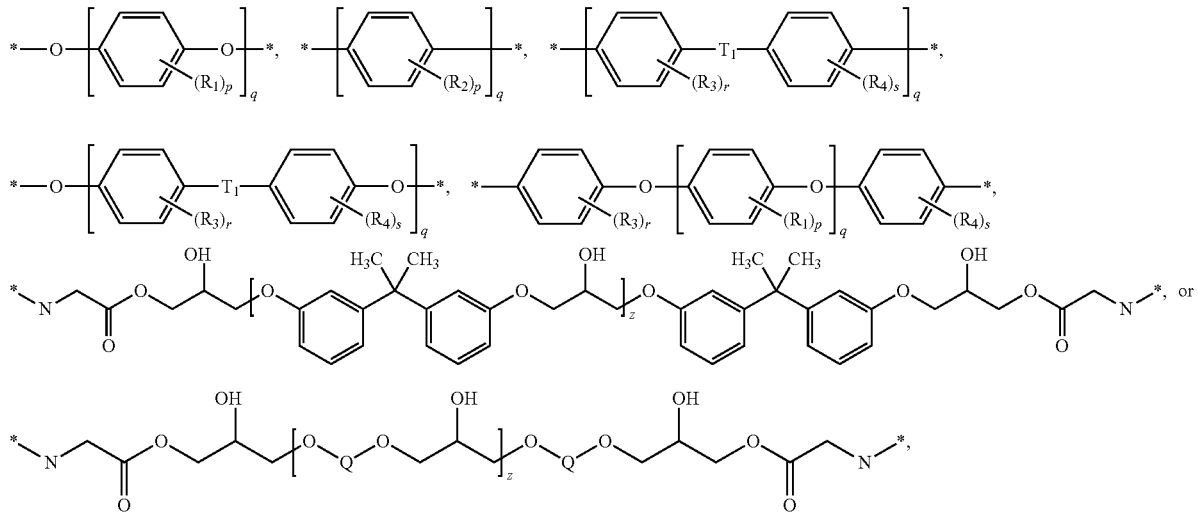

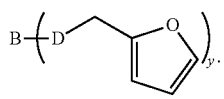
Formula (III)

In Formula (III), y is an integer of 1 to 5, B is a group containing ketone group, amide group, imide group, amine group, imine group, phenyl ether group, or enol ether group, D is a bonding, —O—, —NH—, —$Ar_2$—NH—$(CH_2)_d$—, —$Ar_2$—O—$(CH_2)_b$—, —$Ar_2$—O—$(CH_2)_c$—NH—$(CH_2)_d$—, —$(CH_2)_c$—NH—$(CH_2)_d$—, —$(CH_2)_c$—O—$(CH_2)_d$—, or —$(CH_2)_c$—CH(OH)—$(CH_2)_d$—NH—, $Ar_2$ is substituted or unsubstituted arylene group, c is an integer of 1 to 5, and d is an integer of 0 to 5.

In some embodiments of the disclosure, $Ar_2$ is substituted or unsubstituted phenylene group, biphenylene group, naphthylene group, thienylene group, indolylene group, phenanthrenylene, indenylene group, anthracenylene group, or fluorenylene group. More specifically, $Ar_2$ can be phenylene group, biphenylene group, naphthylene group, thienylene group, indolylene group, phenanthrenylene, indenylene group, anthracenylene group, or fluorenylene group with substitution groups of one to four $C_1$-$C_6$ alkyl groups.

In some embodiments of the disclosure, B can be

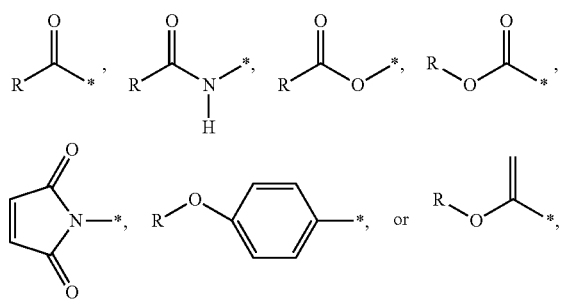

R is hydrogen, halogen, $C_1$-$C_8$ alkyl group, $C_1$-$C_8$ haloalkyl group, $C_5$-$C_{10}$ cycloalkyl group, or $C_6$-$C_{12}$ aryl group, and B is connected to D by the location represented by *. More specifically, B can be

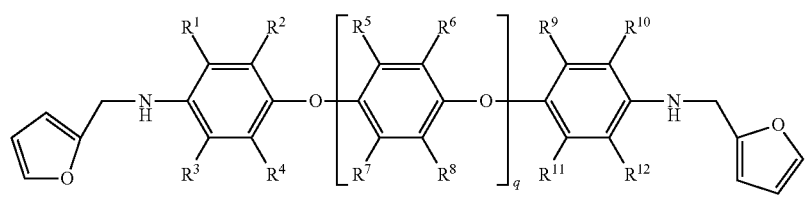

B is connected to D by the location represented by *, wherein $R_8$ is $CH_3$ or $C_2H_5$, t is an integer of 1 to 5, and e is an integer of 1 to 5.

In some embodiments, the furan-group-containing oligomer having a structure represented by Formula (I) and the furan-group-containing compound having a structure represented by Formula (III) in the composition may have a weight ratio of 20:80 to 80:20.

In some embodiments, the equivalent ratio of the total number of furan groups of the at least one furan-group-containing oligomer having a structure represented by Formula (I) and the furan-group-containing compound having a structure represented by Formula (III) to the maleimide group of the bismaleimide compound having a structure represented by Formula (II) is from 0.7:1 to 1:0.5.

One embodiment of the disclosure further provides a reversible crosslinking reactant composition, including (a) oligomer, wherein (a) oligomer has a number average molecular weight of 1000 to 12000, wherein (a) oligomer is an oligomer having a structure represented by Formula (IV), an oligomer having a structure represented by Formula (V), or an oligomer having a first repeating unit and a second repeating unit, wherein the first repeating unit has a structure represented by Formula (VI), the second repeating unit has a structure represented by Formula (VII), and the first repeating unit and the second repeating unit are arranged randomly or in blocks, Formula (IV)

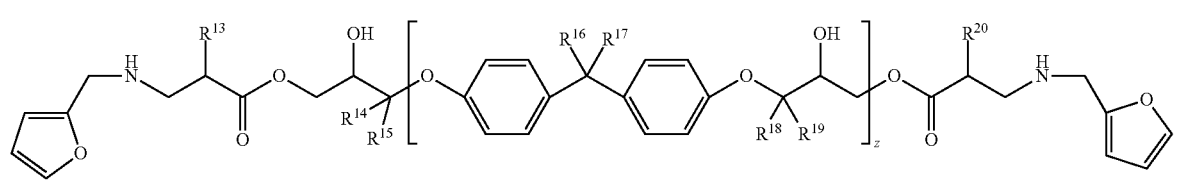

Formula (V)

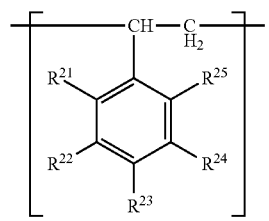

Formula (VI)

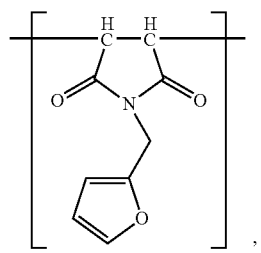

Formula (VII)

wherein each of $R^1$, $R^2$, $R^3$, $R^4$, $R^5$, $R^6$, $R^7$, $R^8$, $R^9$, $R^{10}$, $R^{11}$, and $R^{12}$ is independently hydrogen, $C_{1-6}$ alkyl group, $C_{1-6}$ alkoxy group, or halogen; each of $R^{13}$, $R^{14}$, $R^{15}$, $R^{18}$, $R^{19}$, and $R^{20}$ is independently hydrogen or $C_{1-6}$ alkyl group; each of $R^{16}$ and $R^{17}$ is independently hydrogen, $C_{1-6}$ alkyl group, $C_{5-8}$ cycloalkyl group, $C_{6-12}$ aryl group, $C_{5-10}$ heteroaryl group, or halogen; each of $R^{21}$, $R^{22}$, $R^{23}$, $R^{24}$, and $R^{25}$ is independently hydrogen, $C_{1-6}$ alkyl group, or halogen; q is an integer of 5 to 50; and z is an integer of 5 to 20; and (b) bismaleimide compound having a structure represented by Formula (II):

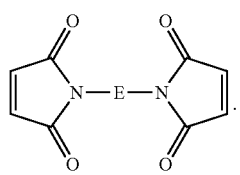

Formula (II)

E is substituted or unsubstituted $C_6$-$C_{25}$ arylene group, $C_7$-$C_{25}$ alkyl aryl group, $C_7$-$C_{25}$ arylalkyl group, $C_6$-$C_{25}$ heteroarylene group, $C_7$-$C_{25}$ acylaryl group, $C_7$-$C_{25}$ alkoxyaryl group, $C_7$-$C_{25}$ acyloxyaryl group, $C_6$-$C_{25}$ arylene ether group, or $C_6$-$C_{25}$ arylene ether group.

In some embodiments of the disclosure, E in Formula (II) is

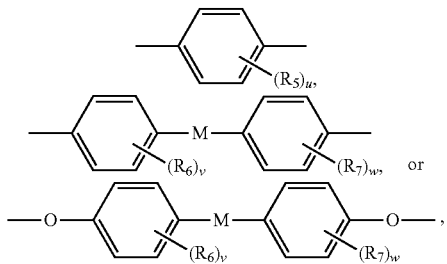

wherein each of u, v, and w is an integer of 1 to 5, each of $R_5$, $R_6$, and $R_7$ is independently $C_1$-$C_5$ alkyl group, M is a bonding, —O—, —S—, $C_1$-$C_{12}$ linear or branched alkyl group, and p is an integer of 1 to 4.

In some embodiments of the disclosure, the reversible crosslinking reactant composition further includes (c) furan-group-containing compound having a structure represented by Formula (III):

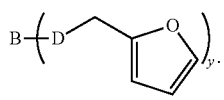

Formula (III)

y is an integer of 1 to 5, B is a group containing ketone group, amide group, imide group, amine group, imine group, phenyl ether group, or enol ether group, D is a bonding, —O—, —NH—, —$Ar_2$—NH—$(CH_2)_d$—, —$Ar_2$—O—$(CH_2)_b$—, —$Ar_2$—O—$(CH_2)_c$—NH—$(CH_2)_d$—, —$(CH_2)_c$—NH—$(CH_2)_d$—, —$(CH_2)_c$—O—$(CH_2)_d$—, or —$(CH_2)_c$—CH(OH)—$(CH_2)_d$—NH—, $Ar_2$ is substituted or unsubstituted arylene group, c is an integer of 1 to 5, and d is an integer of 0 to 5.

In some embodiments of the disclosure, $Ar_2$ is substituted or unsubstituted phenylene group, biphenylene group, naphthylene group, thienylene group, indolylene group, phenanthrenylene, indenylene group, anthracenylene group, or fluorenylene group.

In some embodiments of the disclosure, B is

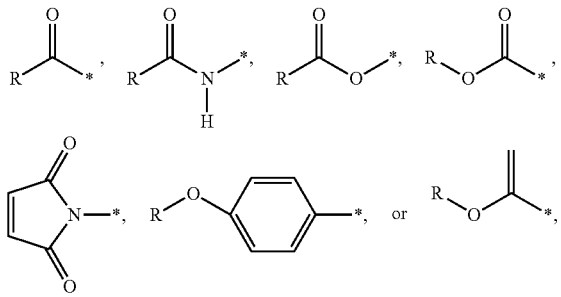

R is hydrogen, halogen, $C_1$-$C_8$ alkyl group, $C_1$-$C_8$ haloalkyl group, $C_5$-$C_{10}$ cycloalkyl group, or $C_6$-$C_{12}$ aryl group, and B is connected to D by the location represented by *.

In some embodiments of the disclosure, B is

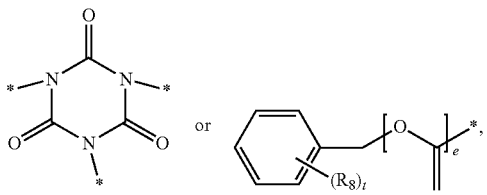

B is connected to D by the location represented by *, wherein $R_8$ is $CH_3$ or $C_2H_5$, t is an integer of 1 to 5, and e is an integer of 1 to 5.

In some embodiments, (a) oligomer and (c) furan-group-containing compound having a structure represented by Formula (III) have a weight ratio of 20:80 to 80:20.

In some embodiments, the equivalent ratio of the total number of furan groups of (a) oligomer and (b) furan-group-containing compound having a structure represented by Formula (III) to the maleimide group of (b) bismaleimide compound having a structure represented by Formula (II) is from 0.7:1 to 1:0.5.

According to embodiments of the disclosure, the composition of the disclosure can be used in copper clad laminate or PCB process. The composition of the disclosure can be used as adhesive, coating, package, composite, or functional film, and further used in several optical and electronic product.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity.

Preparation Examples of Furan-Group-Containing Oligomer

The oligomer having a structure represented by Formula (I-1) (m was 7~200, n was 7~200, and the oligomer had a number average molecular weight of 2000~12000)

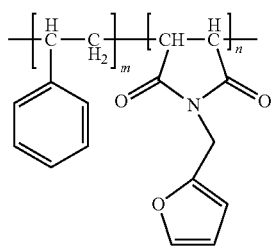

Formula (I-1)

Example 1

60 g of styrene maleic anhydride (SMA, commercially available from Polyscope, weight average molecular weight (Mw):7500) was put into 80 g of dimethylacetamide (DMAc, commercially available from Echo Chemical Co., Ltd) to be pre-dissolved. 29.6 g of furfurylamine (FA, commercially available from Aldrich) was then added into DMAc and SMA, and then heated to 100° C.~160° C. and stirred to react. After completing the reaction, the temperature was cooled to room temperature to obtain an oligomer having a structure represented by Formula (I-1). Subsequently, the physical properties of the oligomer were measured, as shown in Table 1.

Example 2

60 g of styrene maleic anhydride (SMA, commercially available from Polyscope, weight average molecular weight (Mw):9000) was put into 80 g of dimethylacetamide (DMAc) to be pre-dissolved. 22.33 g of furfurylamine (FA, commercially available from Aldrich) was then added into DMAc and SMA, and then heated to 100° C.~160° C. and stirred to react. After completing the reaction, the temperature was cooled to room temperature to obtain an oligomer having a structure represented by Formula (I-1). Subsequently, the physical properties of the oligomer were measured, as shown in Table 1.

Example 3

83 g of styrene maleic anhydride (SMA, commercially available from Polyscope, weight average molecular weight (Mw):10000) was put into 115 g of dimethylacetamide (DMAc) to be pre-dissolved. 40 g of furfurylamine (FA, commercially available from Aldrich) was then added into DMAc and SMA, and then heated to 100° C.~160° C. and stirred to react. After completing the reaction, the temperature was cooled to room temperature to obtain an oligomer having a structure represented by Formula (I-1). Subsequently, the physical properties of the oligomer were measured, as shown in Table 1.

Analysis of Properties and Result

The oligomers prepared in Examples 1 to 3 were analyzed by reflection IR spectroscopy (Spectrum One-54415, PERLIN ELMER) to measure their IR spectra. In the IR spectra data, the —$CO_2$NH character peaks of 1701 cm$^{-1}$ and 1776 cm$^{-1}$ mean that the furfurylamine was grafted on the styrene maleic anhydride to form the maleimide functional group. The C—O—C character peaks of 1006 cm$^{-1}$ and 1068 cm$^{-1}$ and the C=C character peak of 1491 cm$^{-1}$ mean the signals of furan group in the furfurylamine. In addition, the oligomers prepared in Examples 1 to 3 were analyzed by differential scanning calorimeter (Q10, TA Instrument Co., Ltd.) under the standard IPC-TM-650.2.4.24 to measure their glass transfer temperature (Tg), as tabulated in Table 1. The oligomers prepared in Examples 1 to 3 were also analyzed by gel permeation chromatography (RI 830, JASCO) to measure their weight average molecular weight (Mw), as tabulated in Table 1.

TABLE 1

| | Composition | | | Properties | |
|---|---|---|---|---|---|
| | SMA | | | | |
| | Mw | (g) | FA (g) | Tg (° C.) | Mw |
| Example 1 | 7,500 (m: 40, n: 20) | 60 | 29.6 | 121 | 8,700 |
| Example 2 | 9,000 (m40, n: 30) | 60 | 22.33 | 112 | 10,500 |
| Example 3 | 10,000 (m: 30, n: 40) | 83 | 40 | 103 | 11,800 |

The oligomer having a structure represented by Formula (I-2) (x was 5~47, and the oligomer had a number average molecular weight of 1000~6000)

Formula (I-2)

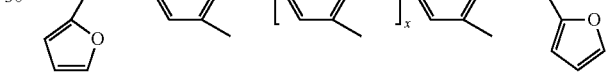

Example 4

60 g of polyphenylene ether (PPE, commercially available from Sabic, Mn:1600) was put into 60 g of dimethylacetamide (DMAc) to be pre-dissolved. 6.9 g of furfurylamine (FA, commercially available from Aldrich) was then added into DMAc and PPE, and then heated to 100° C.~160° C. and stirred to react. After completing the reaction, the temperature was cooled to room temperature to obtain an oligomer having a structure represented by Formula (I-2). Subsequently, the physical properties of the oligomer were measured, as shown in Table 2.

Example 5

60 g of polyphenylene ether (PPE, commercially available from Sabic, Mn:2350) was put into 60 g of dimethylacetamide (DMAc) to be pre-dissolved. 8 g of furfurylamine (FA, commercially available from Aldrich) was then added into DMAc and PPE, and then heated to 100° C.~160° C. and stirred to react. After completing the reaction, the temperature was cooled to room temperature to obtain an oligomer having a structure represented by Formula (I-2). Subsequently, the physical properties of the oligomer were measured, as shown in Table 2.

Analysis of Properties and Result

The oligomers prepared in Examples 4 and 5 were analyzed by reflection IR spectroscopy (Spectrum One-54415, PERLIN ELMER) to measure their IR spectra. In the IR spectra data, the NH character peak of 3200 cm$^{-1}$ to 3400

$cm^{-1}$ means that the furfurylamine was grafted on the polyphenylene ether. The C—O—C character peaks of 1006 $cm^{-1}$ and 1068 $cm^{-1}$ and the C=C character peak of 1491 $cm^{-1}$ mean the signals of furan group in the furfurylamine. In addition, the oligomers prepared in Examples 4 and 5 were analyzed by differential scanning calorimeter (Q10, TA Instrument Co., Ltd.) under the standard IPC-TM-650.2.4.24 to measure their glass transfer temperature (Tg), as tabulated in Table 2. The oligomers prepared in Examples 4 and 5 were also analyzed by gel permeation chromatography (RI 830, JASCO) to measure their weight average molecular weight (Mw), as tabulated in Table 2.

TABLE 2

| | Composition | | Properties | |
|---|---|---|---|---|
| | PPE | | | |
| | Mw | (g) | FA (g) | Tg (° C.) | Mw |
| Example 4 | 1,600 | 60 | 6.9 | 142 | 3,850 |
| Example 5 | 2,350 | 60 | 8 | 152 | 5,210 |

The oligomer having a structure represented by Formula (I-3) (z was 5~20 and the oligomer had a number average molecular weight of 900~3000)

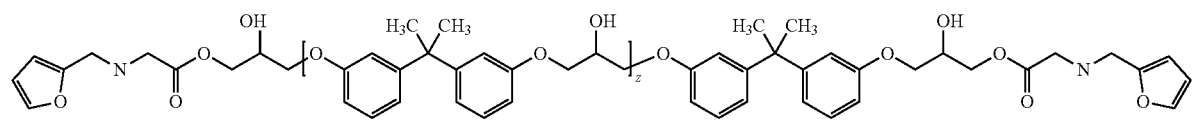

Formula (I-3)

Example 6

50 g of epoxy acrylate oligomer (DOUNLEMER1730, commercially available from Double Bond Chemical) was put into 60 g of dimethylacetamide (DMAc). 10 g of furfurylamine (FA, commercially available from Aldrich) was then added into DMAc and DOUNLEMER1730, and then heated to 100° C.~140° C. and stirred to react. After completing the reaction, the temperature was cooled to room temperature to obtain an oligomer having a structure represented by Formula (I-3). Subsequently, the physical properties of the oligomer were measured, as shown in Table 3.

Analysis of Properties and Result

The oligomer prepared in Example 6 was analyzed by reflection IR spectroscopy (Spectrum One-54415, PERLIN ELMER) to measure its IR spectrum. In the IR spectrum data, the NH character peak of 3200 $cm^{-1}$ to 3400 $cm^{-1}$ means that the furfurylamine was grafted on the epoxy acrylate oligomer. The C—O—C character peaks of 1006 $cm^{-1}$ and 1068 $cm^{-1}$ and the C=C character peak of 1491 $cm^{-1}$ mean the signals of furan group in the furfurylamine. In addition, the oligomer prepared in Example 6 was analyzed by differential scanning calorimeter (Q10, TA Instrument Co., Ltd.) under the standard IPC-TM-650.2.4.24 to measure its glass transfer temperature (Tg), as tabulated in Table 3. The oligomer prepared in Example 6 was also analyzed by gel permeation chromatography (RI 830, JASCO) to measure its weight average molecular weight (Mw), as tabulated in Table 3.

TABLE 3

| | Composition | | | Properties | |
|---|---|---|---|---|---|
| | Epoxy acrylate oligomer | | | | |
| | Mn | (g) | FA (g) | Tg (° C.) | Mw |
| Example 6 | ~850 | 60 | 8.5 | 125.3 | ~850 |

Preparation Examples of Furan-Group-Containing Compound

The compound having a structure represented by Formula (III-1) (T was —CH$_2$—CH(OH)— group (e.g. T was connected to N through CH$_2$) or —CH$_2$—CH$_2$— group)

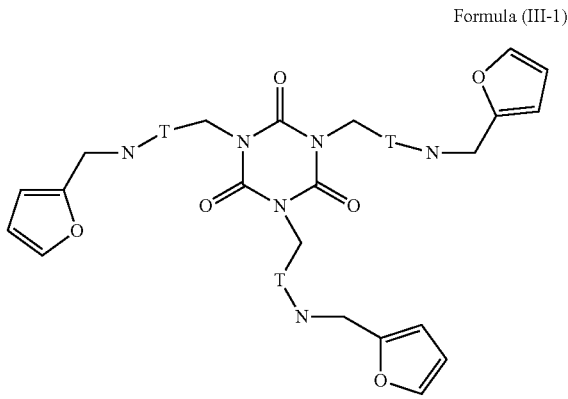

Formula (III-1)

Example 7

50 g of triallyl isocyanurate (TAIC, commercially available from Aldrich) was put into 60 g of dimethylacetamide (DMAc). 19.48 g of furfurylamine (FA, commercially available from Aldrich) was then added into DMAc and TAIC, and then heated to 100° C.~160° C. and stirred to react. After completing the reaction, the temperature was cooled to room temperature to obtain an oligomer having a structure represented by Formula (III-1). Subsequently, the physical properties of the compound were measured, as shown in Table 4.

Example 8

50 g of tris(2,3-epoxy propyl) isocyanurate (TEPIC, commercially available from Nissan Chemical) was put into 60 g of dimethylacetamide (DMAc). 23 g of furfurylamine (FA, commercially available from Aldrich) was then added into DMAc and TEPIC, and then heated to 100° C.~160° C. and stirred to react. After completing the reaction, the temperature was cooled to room temperature to obtain an oligomer having a structure represented by Formula (III-1). Subsequently, the physical properties of the compound were measured, as shown in Table 4.

Analysis of Properties and Result

The compounds prepared in Examples 7 and 8 were analyzed by reflection IR spectroscopy (Spectrum One-54415, PERLIN ELMER) to measure their IR spectra. In the IR spectra data, the NH character peak of 3200 cm$^{-1}$ to 3400 cm$^{-1}$ means that the furfurylamine was grafted on the triallyl isocyanurate or the tris(2,3-epoxy propyl) isocyanurate. The C—O—C character peaks of 1006 cm$^{-1}$ and 1068 cm$^{-1}$ and the C═C character peak of 1491 cm$^{-1}$ mean the signals of furan group in the furfurylamine. In addition, the compounds prepared in Examples 7 and 8 were analyzed by differential scanning calorimeter (Q10, TA Instrument Co., Ltd.) under the standard IPC-TM-650.2.4.24 to measure their glass transfer temperature (Tg), as tabulated in Table 4.

TABLE 4

| | Composition | | | Properties |
|---|---|---|---|---|
| | TAIC(g) | TEPIC(g) | FA (g) | Tg (° C.) |
| Example 7 | 50 | 0 | 19.48 | 143.17 |
| Example 8 | 0 | 50 | 23 | 152 |

Preparation Examples of Reversible Crosslinking Reactant Composition

Compositions Including Only One Type of Furan-Group-Containing Oligomer

Example 9

100.47 g of the oligomer having a structure represented by Formula (I-1) synthesized in Example 1 and 50 g of the bismaleimide compound BMI-1000 (commercially available from K.I. Chemical Industry, molecular weight: 358.35) were reacted at 50° C.~60° C. for 30 minutes to form varnish (reversible crosslinking reactant composition). The varnish was put in an oven and reacted at 170° C.~190° C. to obtain cross-linked composition I.

Example 10

271.2 g of the oligomer having a structure represented by Formula (I-2) synthesized in Example 4 and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition II.

Example 11

40.18 g of the oligomer having a structure represented by Formula (I-1) synthesized in Example 1 and 10 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition III.

Example 12

108.4 g of the oligomer having a structure represented by Formula (I-2) synthesized in Example 4 and 10 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition IV.

Example 13

50.24 g of the oligomer having a structure represented by Formula (I-1) synthesized in Example 1 and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition V.

Example 14

135.6 g of the oligomer having a structure represented by Formula (I-2) synthesized in Example 4 and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition VI.

Analysis of Properties and Result

The cross-linked compositions I to VI prepared in Examples 9 to 14 were analyzed by reflection IR spectroscopy (Spectrum One-54415, PERLIN ELMER) to measure their IR spectra. In the IR spectra data, the original BMI-1000 character peak of 822 cm$^{-1}$ disappeared after the reaction, and the signal intensity of the C—O—C character peak on the furan group of 1068 cm$^{-1}$ was obviously lowered, which means that the cross-linked products were formed. In addition, the cross-linked compositions I to VI prepared in Examples 9 to 14 were analyzed by differential scanning calorimeter (Q10, TA Instrument Co., Ltd.) under the standard IPC-TM-650.2.4.24 to measure their glass transfer temperature (Tg), as tabulated in Table 5. The cross-linked compositions I to VI prepared in Examples 9 to 14 were respectively sampled as 5 mg and analyzed by differential scanning calorimeter (Q10, TA Instrument Co., Ltd.), in which each of the samples was heated to 350° C. at a heating rate of 5° C./min to measure the reversible crosslinking temperature (Tr) of the cross-linked compositions I to VI prepared in Examples 9 to 14, as tabulated in Table 5. As seen in the reversible crosslinking temperature (Tr) in Table 5, the cross-linked compositions in Examples could be stable at a high temperature of at least 160° C.

TABLE 5

| | Composition | | | Properties | |
|---|---|---|---|---|---|
| | (a) furan-group-containing oligomer (g) | | (b) bismaleimide (g) | | |
| | Formula (I-1) | Formula (I-2) | BMI-1000 | molar ratio | Tg (° C.) | Tr (° C.) |
|---|---|---|---|---|---|---|
| Example 9 | 100.47 | | 50 | 1/1 | 168 | 230 |
| Example 10 | | 271.2 | 50 | 1/1 | 154 | 230 |
| Example 11 | 40.18 | | 10 | 2/1 | 175 | 220 |
| Example 12 | | 108.4 | 10 | 2/1 | 168 | 230 |
| Example 13 | 50.24 | | 50 | 1/2 | 145 | 180 |
| Example 14 | | 135.6 | 50 | 1/2 | 132 | 161 |

Compositions Including a Plurality Types of Furan-Group-Containing Oligomers/Compounds Example 15

54.24 g of the oligomer having a structure represented by Formula (I-1) synthesized in Example 1, 135.6 g of the oligomer having a structure represented by Formula (I-2) synthesized in Example 4, and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition VII.

Example 16

54.24 g of the oligomer having a structure represented by Formula (I-1) synthesized in Example 1, 42.38 g of the compound having a structure represented by Formula (III-1) synthesized in Example 7, and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition VIII.

Example 17

135.6 g of the oligomer having a structure represented by Formula (I-2) synthesized in Example 4, 42.38 g of the compound having a structure represented by Formula (III-1) synthesized in Example 7, and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition IX.

Example 18

33.5 g of the oligomer having a structure represented by Formula (I-1) synthesized in Example 1, 90.4 g of the oligomer having a structure represented by Formula (I-2) synthesized in Example 4, 28.3 g of the compound having a structure represented by Formula (III-1) synthesized in Example 7, and 50 g of the bismaleimide compound BMI-1000 (commercially available from K.I. Chemical Industry) were reacted at 50° C.~60° C. for 30 minutes to form varnish (reversible crosslinking reactant composition). The varnish was put in an oven and reacted at 170° C.~190° C. to obtain cross-linked composition X.

Analysis of Properties and Result

The cross-linked compositions VII to X prepared in Examples 15 to 18 were analyzed by reflection IR spectroscopy (Spectrum One-54415, PERLIN ELMER) to measure their IR spectra. In the IR spectra data, the original C=C character peak on BMI-1000 of 822 $cm^{-1}$ disappeared after the reaction, and the signal intensity of the C—O—C character peak on the furan group of 1068 $cm^{-1}$ was obviously lowered, which means that the cross-linked products were formed. In addition, the cross-linked compositions VII to X prepared in Examples 15 to 18 were analyzed by differential scanning calorimeter (Q10, TA Instrument Co., Ltd.) under the standard IPC-TM-650.2.4.24 to measure their glass transfer temperature (Tg), as tabulated in Table 6. The cross-linked compositions VII to X prepared in Examples 15 to 18 were respectively sampled as 5 mg and analyzed by differential scanning calorimeter (Q10, TA Instrument Co., Ltd.), in which each of the samples was heated to 350° C. at a heating rate of 5° C./min to measure the reversible crosslinking temperature (Tr) of the cross-linked compositions VII to X prepared in Examples 15 to 18, as tabulated in Table 6. As seen in the reversible crosslinking temperature (Tr) of Table 6, the cross-linked compositions in Examples could be stable at a high temperature of at least 160° C.

TABLE 6

| | Composition | | | | | Properties | |
|---|---|---|---|---|---|---|---|
| | (a) furan-group-containing oligomer (g) | | | (b) bismaleimide | | | |
| | Formula (I-1) | Formula (I-2) | Formula (III-1) | (g) BMI-1000 | molar ratio | Tg (° C.) | Tr (° C.) |
| Example 15 | 54.24 | 135.6 | | 50 | 1/1 | 185 | 200 |
| Example 16 | 54.24 | | 42.38 | 50 | 1/1 | 169 | 250 |
| Example 17 | | 135.6 | 42.38 | 50 | 1/1 | 251 | 300 |
| Example 18 | 33.5 | 90.4 | 28.3 | 50 | 1/1 | 237 | 290 |

Reversible Reaction Test and Result

The cross-linked compositions I to X prepared in Examples 9 to 18 were crushed. The cross-linked compositions were heated to about 250° C.~300° C. to crack the crosslinking bondings and reverse back to varnish state, and then cooled to 60° C.~80° C. to further harden to bulks. The bulks were analyzed by reflection IR spectroscopy (Spectrum One-54415, PERLIN ELMER) to measure their IR spectra. In the IR spectra data, the original C=C character peak on BMI-1000 of 822 cm$^{-1}$ reappeared, and the signal intensity of the C—O—C character peak on the furan group of 1068 cm$^{-1}$ was obviously enhanced, which means that the crosslinking bondings of the cross-linked compositions were cracked, thereby recovering back to the compositions of furan group-containing oligomer and/or compound and BMI-1000.

Discussion of Analysis Results

For the reversible crosslinking reactant compositions in Examples, the two maleimide groups of the bismaleimide compound could react with the furan groups of two furan group-containing oligomer or compound through the 1,2-addition reaction. When the steric structure achieved a specific temperature, the bondings formed from the 1,2-addition reaction would be cracked, thereby breaking the bridge between the furan group-containing oligomer/compound and the bismaleimide compound for recovering back to original reactants. The above properties are beneficial to recycle and reuse the compositions. According to the result of the Examples, the reversible crosslinking reactant compositions of the disclosure had a stable structure, high thermal resistance, and high reversible temperature, which were beneficial for use in high-temperature processes. For example, the composition serving as the insulation resin material for PCB should be intact during the reflow process, such that the reversible temperature of the composition was preferably higher than or equal to 250° C.

Synthesis and Analysis of Composite Material

Example 19

33.5 g of the oligomer having a structure represented by Formula (I-1) synthesized in Example 1, 90.4 g of the oligomer having a structure represented by Formula (I-2) synthesized in Example 4, 28.3 g of the compound having a structure represented by Formula (III-1) synthesized in Example 7, and 50 g of the bismaleimide compound BMI-1000 (commercially available from K.I. Chemical Industry) were added to 75 g of dimethylacetamide (DMAc), and reacted at 50° C.~60° C. for 30 minutes to form varnish (reversible crosslinking reactant composition). A glass fiber cloth was impregnated in the varnish, and then backed at 140° C.~170° C. to prepare a prepreg. The prepregs were laminated with copper foil to form copper clad laminate.

Comparative Example 100 wt % of Epoxy resin 828 (BE-188, commercially available from Chang Chun Chemical Co., Ltd.), 5 phr of dicyandiamide (commercially available from Echo Chemical Co., Ltd), and 500 ppm of 2-methylimidazole (2-MI, commercially available from Echo Chemical Co., Ltd.) were added to methyl ethyl ketone (MEK, commercially available from Echo Chemical Co., Ltd) to prepare a varnish with a solid content of 70%. A glass fiber cloth was impregnated in the varnish, and then backed at 170° C. to prepare a prepreg. The prepregs were laminated with copper foil to form copper clad laminate. The lamination process was performed at a temperature of 170° C.~190° C. for 1 hours to 2 hours under a pressure of 350 psi~450 psi. The prepared copper clad laminate was FR-4 plate for general PCB.

Analysis of Properties and Result

The copper clad laminates in Examples 19 and Comparative Example were analyzed by differential scanning calorimeter (Q10, TA Instrument Co., Ltd.) under the standard IPC-TM-650.2.4.24 to measure their glass transfer temperature (Tg), as tabulated in Table 7. The copper clad laminates in Examples 19 and Comparative Example were analyzed by thermomechanical analyzer (Q400, TA Instrument Co., Ltd.) under the standard IPC-TM-650.2.4.24 to measure their coefficient of thermal expansion (CTE), as tabulated in Table 7. The copper clad laminates in Examples 19 and Comparative Example were analyzed by thermogravimetric analysis (Q500, TA Instrument Co., Ltd.) under the standard IPC-TM-650 2.3.40 to measure their degradation temperature (Td), as tabulated in Table 7. The copper clad laminates in Examples 19 and Comparative Example were respectively sampled as 5 mg and analyzed by differential scanning calorimeter (Q10, TA Instrument Co., Ltd.), in which each of the samples was heated to 350° C. at a heating rate of 5° C./min to measure the reversible crosslinking temperature (Tr) of the copper clad laminates in Examples 19 and Comparative Example, as tabulated in Table 7. The copper clad laminates in Examples 19 and Comparative Example were analyzed by resonant cavity type microwave dielectrometer (AET company, Japan) under the standard JIS-compliant 1641 to measure their dielectric constant (Dk) and dissipation factor (Df), as tabulated in Table 7. As shown in Table 7, the copper clad laminates in Example 19 and Comparative Example had similar dielectric constant and similar dissipation factor. Compared to Comparative Example, the copper clad laminate in Example 19 had a reversible crosslinking temperature of 300° C. The resin in the copper clad laminate in Example 19 can be reversible cross-linked by heating to about 300° C., thereby forming the furan-group-containing oligomer and/or compound and the bismaleimide compound for being recycled.

TABLE 6

|  | Tg (° C.) | XY-CTE (ppm/° C.) | Td (° C.) | Tr (° C.) | Dk | Df |
|---|---|---|---|---|---|---|
| Example 19 | 180~212 | 16~20 | 360 | 300 | 3.75 | 0.012 |
| Comparative Example | 140 | 30 | 350 | none | 4.2 | 0.015 |

Reversible Reaction Test and Result

The copper clad laminate in Example 19 was etched to remove the copper foils, and then put into a solution of about 250° C. to 300° C. to dissolve and recycle the composition. The recycled resin composition was collected and analyzed by reflection IR spectroscopy (Spectrum One-54415, PERLIN ELMER) to measure its IR spectrum. In the IR spectrum data, the C=C character peak on BMI-1000 of 822 cm$^{-1}$ reappeared, and the signal intensity of the C—O—C character peak on the furan group of 1068 cm$^{-1}$ was obviously enhanced, which means that the crosslinking bondings of the resin compositions were cracked, thereby recovering back to the original furan group-containing oligomer or compound and BMI-1000. In addition, the recycled resin composition was cured again, and the cured resin composition had the same Tg as that of the cured original resin composition (Example 18). It further proves that the composite material in Example 19 can be recycled to be reused.

Discussion of Analysis Results

The composites prepared by methods of Examples included reversible crosslinking reactant compositions, thereby increasing the recycling ratio of the composites. For example, utilizing the compositions with a reversible crosslinking temperature higher than or equal to 250° C. may improve the recycling ratio of PCB, therefore reducing the $CO_2$ emission amounts. In addition, the recycled compositions can be repeatedly used as the insulation resin during fabricating PCB or sub-quality raw material for achieving the circular economy.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A reversible crosslinking reactant composition, comprising:
   at least one furan-group-containing oligomer having a structure represented by Formula (I) and;
   a bismaleimide compound having a structure represented by Formula (II):

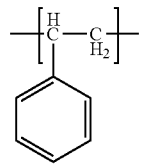

Formula (I)

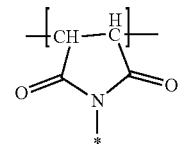

Formula (II)

wherein the equivalent ratio of the furan group of the furan-group-containing oligomer having a structure represented by Formula (I) to the maleimide group of the bismaleimide compound having a structure represented by Formula (II) is from 0.5:1 to 1:0.5,
wherein x is an integer of 1 to 5, A is

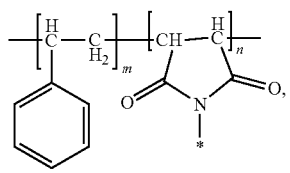

in which the repeating unit

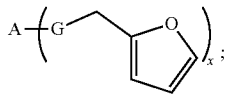

and the repeating unit

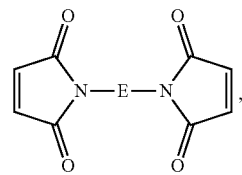

are arranged in order or random, wherein the location represented by * is connected to G, m is an integer of 7 to 200, n is an integer of 7 to 200, G is a bonding, —O—, —NH—, —Ar—NH—$(CH_2)_b$—, —Ar—O—$(CH_2)_b$—, —Ar—O—$(CH_2)_a$—NH—$(CH_2)_b$—, —$(CH_2)_a$—NH—$(CH_2)_b$—, —$(CH_2)_a$—O—$(CH_2)_b$—, or —$(CH_2)_a$—CH(OH)—$(CH_2)_b$—NH—, Ar is substituted or unsubstituted arylene group, a is an integer of 1 to 5, b is an integer of 0 to 5, and the furan-group-containing oligomer having a structure represented by Formula (I) has a number average molecular weight of 1000 to 12000,
   wherein E is substituted or unsubstituted $C_6$-$C_{25}$ arylene group, $C_7$-$C_{25}$ alkyl aryl group, $C_7$-$C_{25}$ arylalkyl group, $C_6$-$C_{25}$ heteroarylene group, $C_7$-$C_{25}$ acylaryl group, $C_7$-$C_{25}$ alkoxyaryl group, $C_7$-$C_{25}$ acyloxyaryl group, $C_6$-$C_{25}$ arylene ether group, or $C_6$-$C_{25}$ arylene ether group.

2. The reversible crosslinking reactant composition as claimed in claim 1, wherein Ar is substituted or unsubstituted phenylene group, biphenylene group, naphthylene group, thienylene group, indolylene group, phenanthrenylene, indenylene group, anthracenylene group, or fluorenylene group.

3. The reversible crosslinking reactant composition as claimed in claim 1, wherein Ar is phenylene group, biphenylene group, naphthylene group, thienylene group, indolylene group, phenanthrenylene, indenylene group, anthracenylene group, or fluorenylene group with substitution groups of one to four $C_1$-$C_6$ alkyl groups.

4. The reversible crosslinking reactant composition as claimed in claim 1, wherein E is
   wherein each of u, v, and w is an integer of 1 to 5, each of $R_5$, $R_6$, and $R_7$ is independently $C_1$-$C_5$ alkyl group, M is a bonding, —O—, —S—, or $C_1$-$C_{12}$ linear or branched alkyl group, and p is an integer of 1 to 4.

5. The reversible crosslinking reactant composition as claimed in claim 1, further comprising a furan-group-containing compound having a structure represented by Formula (III):

Formula (III)

wherein y is an integer of 1 to 5, B is a group containing ketone group, amide group, imide group, amine group, imine group, phenyl ether group, or enol ether group, D is a bonding, —O—, —NH—, —Ar$_2$—NH—(CH$_2$)$_d$—, —Ar$_2$—O—(CH$_2$)$_b$—, —Ar$_2$—O—(CH$_2$)$_c$—NH—(CH$_2$)$_d$—, —(CH$_2$)$_c$—NH—(CH$_2$)$_d$—, —(CH$_2$)$_c$—O—(CH$_2$)$_d$—, or —(CH$_2$)$_c$—CH(OH)—(CH$_2$)$_d$—NH—, Ar$_2$ is substituted or unsubstituted arylene group, c is an integer of 1 to 5, and d is an integer of 0 to 5.

6. The reversible crosslinking reactant composition as claimed in claim 5, wherein Ar$_2$ is substituted or unsubstituted phenylene group, biphenylene group, naphthylene group, thienylene group, indolylene group, phenanthrenylene, indenylene group, anthracenylene group, or fluorenylene group.

7. The reversible crosslinking reactant composition as claimed in claim 5, wherein Ar$_2$ is phenylene group, biphenylene group, naphthylene group, thienylene group, indolylene group, phenanthrenylene, indenylene group, anthracenylene group, or fluorenylene group with substitution groups of one to four C$_1$-C$_6$ alkyl groups.

8. The reversible crosslinking reactant composition as claimed in claim 5, wherein B is

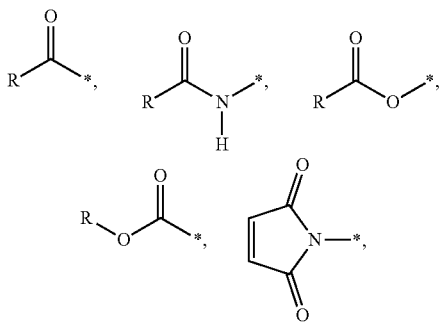

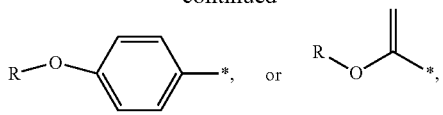

R is hydrogen, halogen, C$_1$-C$_8$ alkyl group, C$_1$-C$_8$ haloalkyl group, C$_5$-C$_{10}$ cycloalkyl group, or C$_6$-C$_{12}$ aryl group, and B is connected to D by the location represented by *.

9. The reversible crosslinking reactant composition as claimed in claim 5, wherein B is

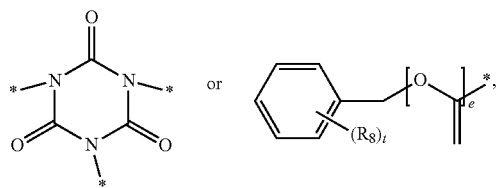

B is connected to D by the location represented by *, wherein R$_8$ is CH$_3$ or C$_2$H$_5$, t is an integer of 1 to 5, and e is an integer of 1 to 5.

10. The reversible crosslinking reactant composition as claimed in claim 5, wherein the at least one furan-group-containing oligomer having a structure represented by Formula (I) and the furan-group-containing compound having a structure represented by Formula (111) have a weight ratio of 20:80 to 80:20.

11. The reversible crosslinking reactant composition as claimed in claim 5, wherein the equivalent ratio of the total number of furan groups of the at least one furan-group-containing oligomer having a structure represented by Formula (I) and the furan-group-containing compound having a structure represented by Formula (111) to the maleimide group of the bismaleimide compound having a structure represented by Formula (II) is from 0.7:1 to 1:0.5.

* * * * *